United States Patent [19]

Nguyen

[11] Patent Number: 5,871,520
[45] Date of Patent: Feb. 16, 1999

[54] RADIO FREQUENCY COMMUNICATION SYSTEM FOR COMMUNICATING WITH A PLURALITY OF TANNING BEDS

[76] Inventor: Hap Nguyen, 17461 Pleasant Ct., Fountain Valley, Calif. 92708

[21] Appl. No.: 728,250

[22] Filed: Oct. 8, 1996

[51] Int. Cl.$^6$ ....................................................... A61N 5/06
[52] U.S. Cl. ................................ 607/88; 607/94; 368/10; 368/108
[58] Field of Search ........................... 607/88–89, 90–91, 607/94; 368/10, 108

[56] References Cited

U.S. PATENT DOCUMENTS

| | | | |
|---|---|---|---|
| 4,980,900 | 12/1990 | Welton | 368/10 X |
| 5,363,347 | 11/1994 | Nguyen | 607/88 X |
| 5,565,857 | 10/1996 | Lee . | |

Primary Examiner—Jeffrey R. Jastrzab
Assistant Examiner—Ryan Carter
Attorney, Agent, or Firm—John P. Halvonik

[57] ABSTRACT

The invention is a remote controlled tanning bed salon that controls the operation of a plurality of tanning beds from a centrally located transceiver. A person wishing to use a tanning bed in the system will input a card having magnetic information coded onto a magnetic strip into a central unit. The central unit will read the information on the strip and determine if such information as to whether the user has already used the tanning bed within a recent time period, how much credit on the account, etc. Once the information has been verified by the central unit one of the tanning beds will be made operable by sending a message by a radio frequency signal to one of the tanning beds. Information concerning which tanning bed is to be used and the length of time of the tanning session are included in the message that is sent from the central unit.

1 Claim, 4 Drawing Sheets

RADIO FREQUENCY COMMUNICATION SYSTEM FOR COMMUNICATING WITH A PLURALITY OF TANNING BEDS

FIELD AND BACKGROUND OF THE INVENTION

The invention relates to the field of tanning beds having a system for automatically operating the tanning beds from a centralized unit. Such a system allows members that subscribe to the system to utilize the tanning beds by use of magnetic cards and readers that belong to the user and are used to operate one of the tanning beds. More particularly, the invention relates to the idea of controlling such a plurality of tanning beds by means of radio frequency signals that are sent from a central unit in order to control individual tanning bed units in the system. The central unit will process information from the magnetic strip cards and then enable one of the tanning beds for use by the customer.

DESCRIPTION OF THE PRIOR ART

The invention represents an improvement on the applicant's previously issued U.S. Pat. No. 5,363,347 directed toward a vending tanning system that utilizes a system of cards having identification means, such as magnetic or optical strips, in order to identify individuals who belong to the tanning salon and who may then enable one of the tanning beds when they wish to get a tan.

It is believed that the use of a radio frequency system that can control a plurality of such tanning beds from a centralized location offers advantages over the prior art. Such beds may be controlled without having to resort to wire based electric communications with the subsequent dangers that this entails. Such dangers include the possibility of electric shock to a repairman and having a much easier method of repositioning individual tanning beds in such a system without having to move or rewire the current wiring system. It is also believed that the use of a RF type of control system will make the installation of the tanning units in the system easier.

SUMMARY OF THE INVENTION

The invention is a remote controlled tanning bed salon system having a centralized unit for processing information from storage units based on cards. The central unit will read the information on the cards and identify the particular individual and then determine such information as: whether that individual has recently used the system; whether his account has credit, etc. Once the central unit determines that the user is allowed to use the system it then makes one of the tanning beds operable by means of sending radio frequency (RF) signals that control the operation of one of the tanning beds.

Once the information has been verified by the central unit one of the tanning beds will be made operable by sending a message by a radio frequency signal to one of the tanning beds. Information concerning which tanning bed is to be used and the length of time of the tanning session are included in the RF message that is sent from the central unit.

It is an object of the invention to provide a plurality of tanning beds that may communicate with a centralized unit in order to minimize the number and the danger of wire connections in such a system.

Another object of the invention is to provide a tanning bed salon system that can control the operation of a plurality of tanning beds from a centralized unit that will respond to the individual tanning beds by means of radio frequency signals.

Other objectives of the invention will become apparent to those skilled in the art once the invention has been shown and described.

DESCRIPTION OF THE PREFERRED EMBODIMENT

Figure 1:
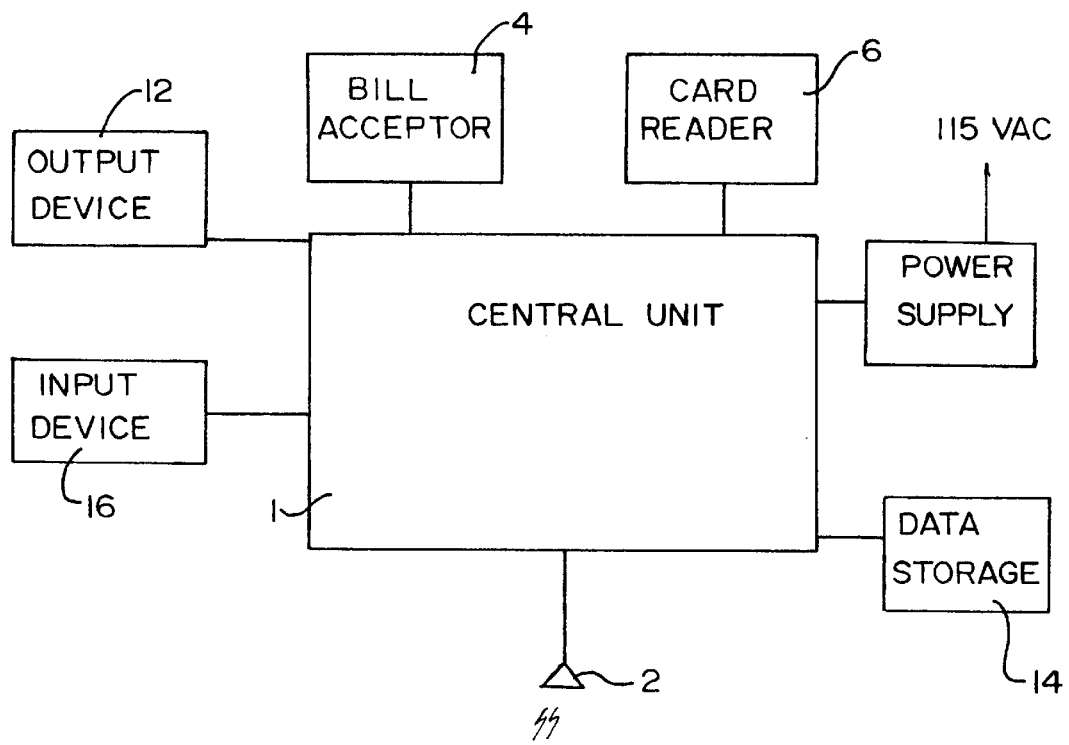
FIG. 1 Overall set up of the system.
Figure 1:
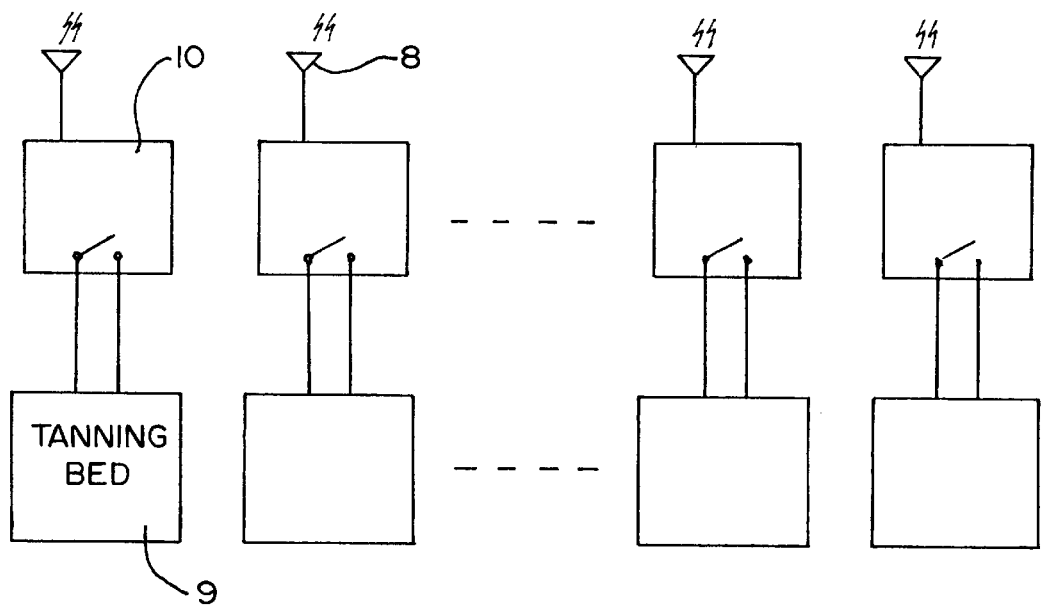

The overall set up the system is as shown in FIG. 1. The operations that go on at the central unit may use the same or similar operations already described in applicant's previously issued U.S. patent. Such operations in general include the central unit identifying the user by an information strip that is on an personal card that has been issued to each member that belongs to the tanning salon. The user would insert his card into a card reader 6 that is in connection with the central unit. The central unit can identify the member by the information on the strip by comparing this to data stored in a memory location 14. The central unit can also determine whether the user has credit on his account, and how much time he is allowed to use the tanning salon for a particular week or month or whatever time period based on the information in memory.

Figure 2:
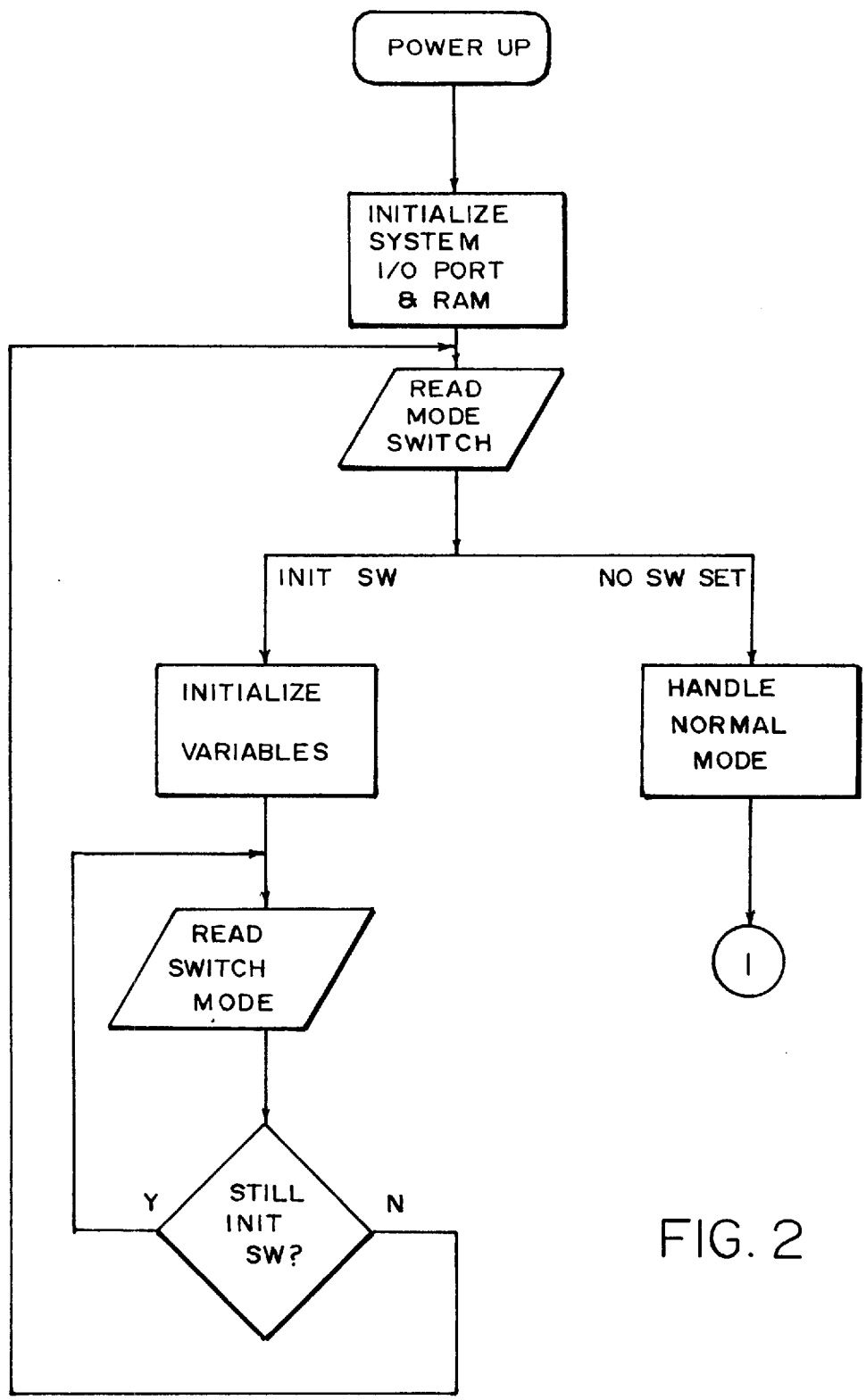
FIG. 2 Flow chart detailing the software program that runs the system.
Figure 3:
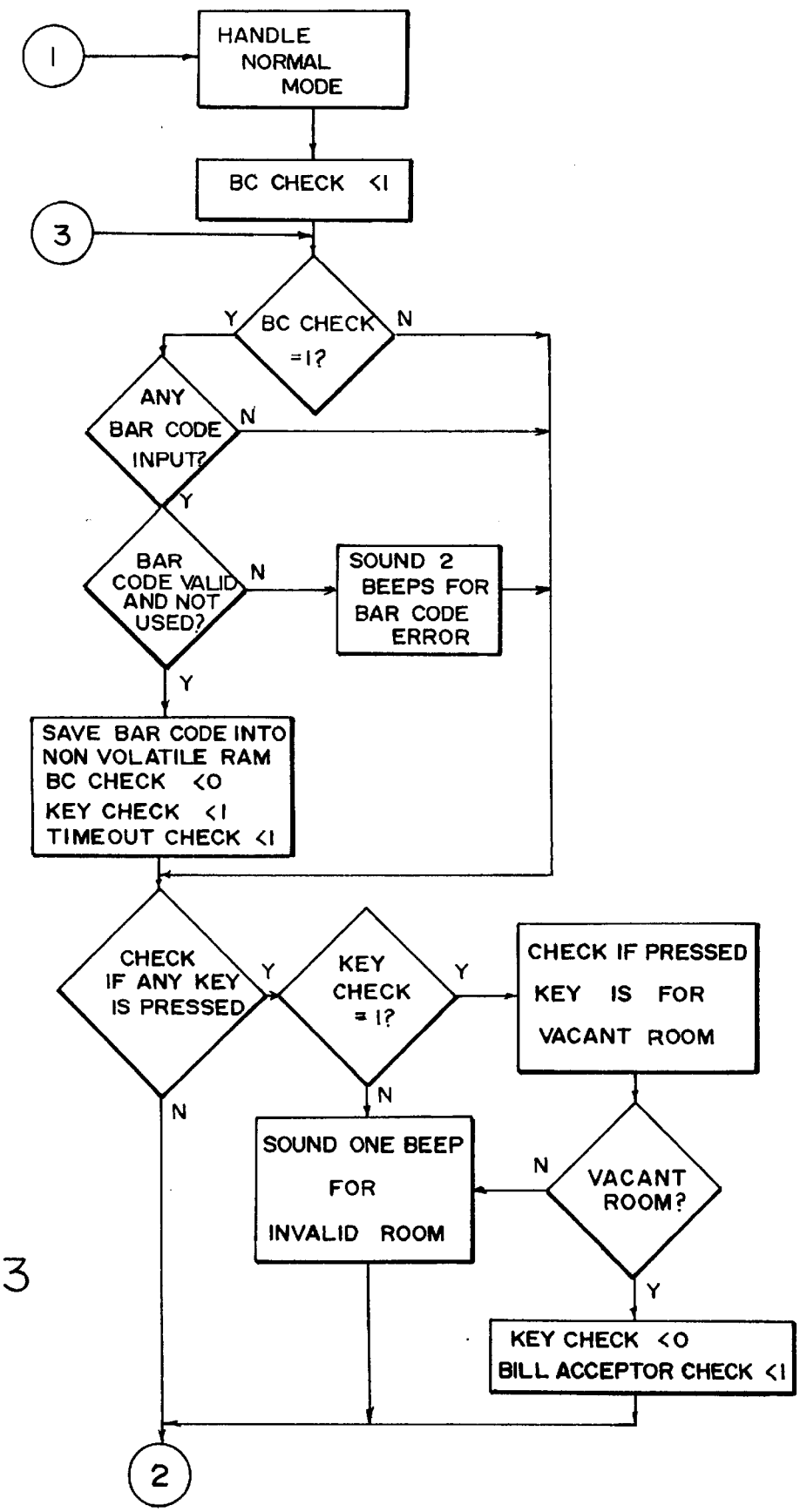
FIG. 3 continuation of FIG. 2 software program.
Figure 4:
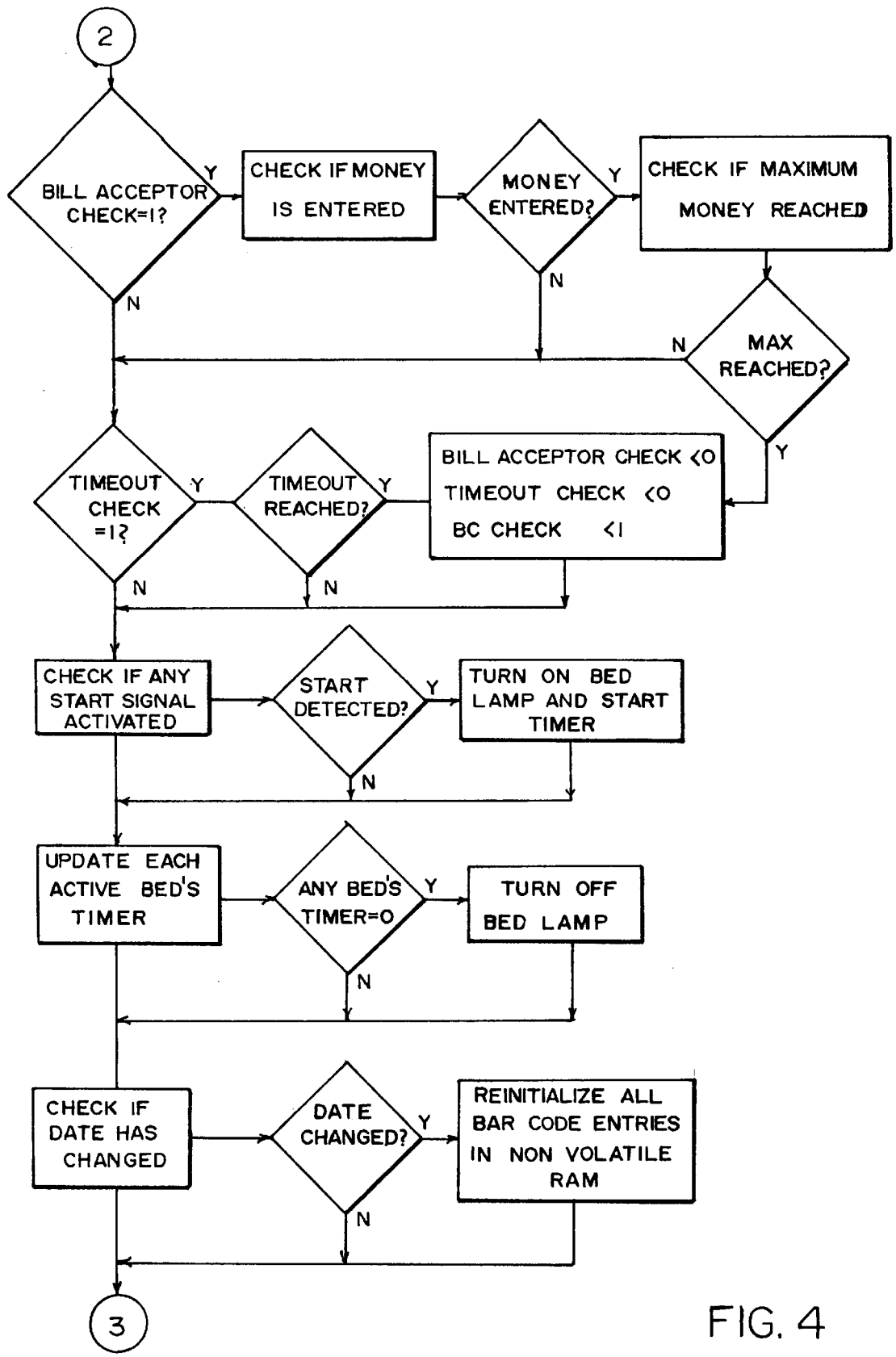
FIG. 4 continuation of FIG. 3.

Once the central unit makes such an identification it can then make operable one of the tanning bed units 9 by a radio frequency signal sent by a transmitter 2 (or transceiver) and then issue instructions to the individual in order to direct him/her to that tanning bed that is now operable for the member. The instructions may be displayed on an output device 12 that may be e.g. an LCD (liquid crystal device) or LED (light emitting diode) device or simlar device that displays information based on instructions it receives from unit 1. A software program may be used to control the operation of the card reader at the central location. Such a program may be viewed as a flow chart as seen in FIGS. 2–4.

The central unit may be broadcast such controls signals on several different frequencies so that different tanning bed units may be set to receive signals via transceivers 8 (or similar means for receiving RF signals) on different radio frequencies. This will decrease the chances for signals to get crossed and will make sure that the proper tanning bed has been made operable for that individual.

Once the user has been approved by the central unit for tanning, he or she may select the time limit for the tanning session that they wish to have. The user may select from one or more rooms that may vary in length of time. This may be by means of an input device 16 in connection with the central unit. Such rooms may be priced differently and the selection of such a room will result in a debit in the corresponding amount from the user's account. Again, account information may be stored in data storage device 14. The central unit may also have a bill acceptor 4 in connection with the unit in order to accept currency and/or make change in order for the user to pay for the tanning session by cash payment at the central unit.

It is believed that several tanning beds may be preset for different tanning times. E.g. one bed can be for a 60 minute session another bed can be fixed for only a 30 minute session, etc. An individual who has already used, say, 30 minutes of available tanning time for that week would be directed by the central unit to go that tanning bed that only has a 30 minute session. This is believed to be a useful and safe way to utilize the system. The central unit can determine how much time an individual has spent in tanning time at the salon for a given time period, say a week, by determining how much time that user has previously used as such information for that week will be stored in memory device 14. By verifying the information on the card, the central unit can determine that the individual is allowed, say an additional 30 minutes for that week, but no more. In this manner, the system can provide a built in safeguard to prevent members from being exposed to too much light for a particular time period.

The central unit may be equipped with a remote control unit that operates as a transceiver. This remote control may have for example, a 6 position DIP switch (dual inline package) in order that different settings can be set on the DIP switching order to communicate with up to a maximum of 64 separate tanning beds.

A micro processor based printed circuit board may be used as a command center for the system at 1. It may come with a microprocessor chip, a ROM (read only memory) or EPROM (erasable read only memory) where the program that runs the central unit may be stored. RAM (random access memory) unit may be used to temporarily store information pertaining to an individuals daily or weekly tanning activity at location 14. The unit may also have a Non volatile RAM in order to keep track of the calendar date, the time of day, and to store user information, the number of sessions used by the system, the amount of money taken in by the system etc.

The transceiver 8 at the tanning bed will have a means to accept an addressable signal sent by transmitter 2 in connection with the central unit. Both the central unit and the tanning may have transceivers that send and receive information in the form of RF signals back and forth to one another. The tanning bed may be made operable upon receiving the proper signal from the central unit.

The receiving section 8 and 10 at each tanning bed may be permanently powered by either a battery or an AC adapter. It may have with an addressable relay 10 (mechanical or solid state) that may be activated by the coded RF signal that is sent by the central unit. Such a relay can control the operation of the tanning bed by making it operable.

I claim:

1. A system for operating a plurality of tanning beds for users of a tanning salon, said system comprising: a central unit for receiving information about the user from a card having an information strip, said central unit having a means to verify the user's identity and for determining the amount of time that said user has spent tanning within the salon in a recent period of time, said central unit having a means to transmit a radio frequency signal for making operable one of said plurality of tanning beds, said plurality of tanning beds being divided into at least two groups of said beds, each of said groups being preset to emit tanning light for a predetermined tanning time period distinct from the other of said groups, said central unit having a means for keeping a record of which group of tanning beds have a given tanning time period and for matching said individual with a given tanning bed according to the user's tanning needs, said central unit in connection with an output means for providing information to direct the user to a particular tanning bed that has a predetermined tanning time corresponding to the user's needs; said central unit having a means to make operable said tanning bed having a time that is appropriate for the user.

* * * * *